Feb. 16, 1954 E. S. BOERNER Plant Pat. 1,251
ROSE PLANT
Filed Feb. 24, 1953
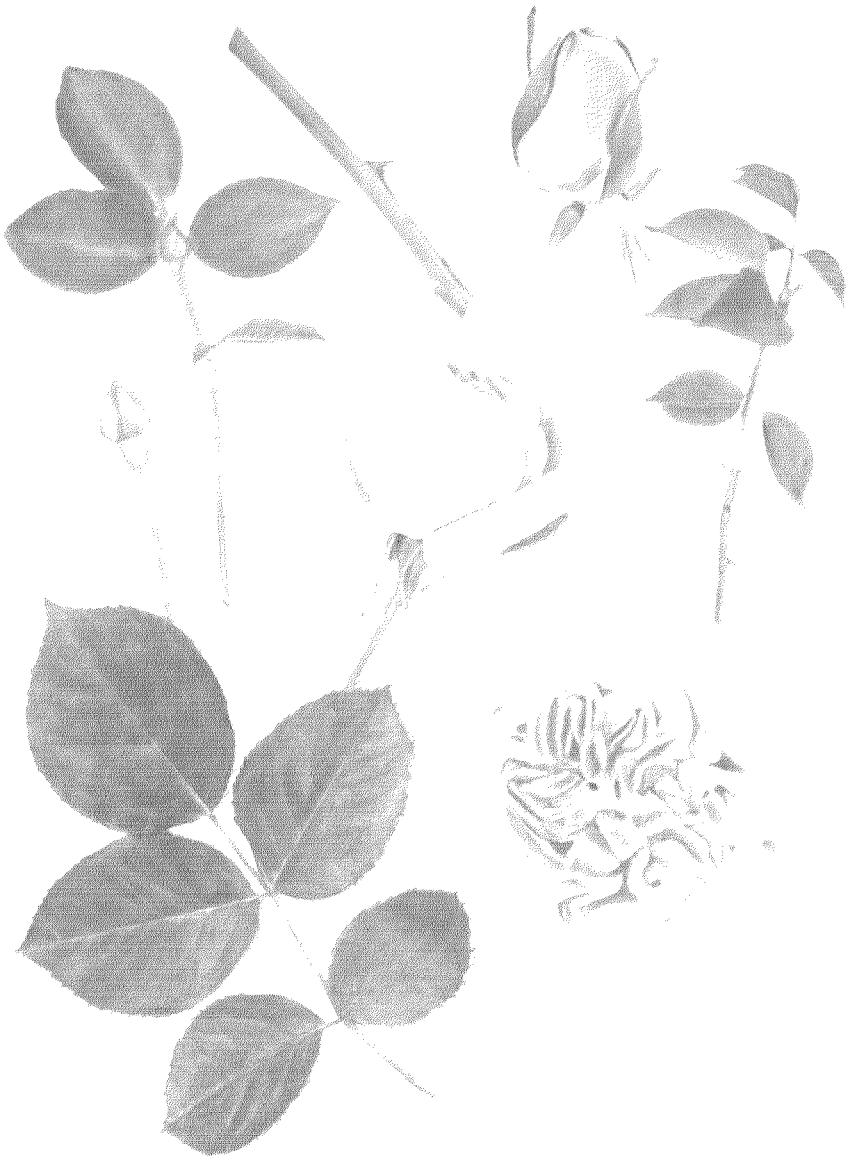
Inventor
E. S. Boerner
By: Robert Robb
Attorneys Patented Feb. 16, 1954 Plant Pat. 1,251

UNITED STATES PATENT OFFICE 1,251

ROSE PLANT

Eugene S. Boerner, Newark, N. Y., assignor to Jackson & Perkins Company, Newark, N. Y., a corporation of New York Application February 24, 1953, Serial No. 338,628

1 Claim. (Cl. 47—61)

The present invention relates to a new and distinct variety of rose plant of the hybrid tea class, which was originated by me by crossing an unnamed and unpatented seedling of the variety "Diamond Jubilee" (Plant Patent No. 824) with the variety "Serenade" (Plant Patent No. 852).

The primary objective of this cross was to produce a new variety of rose plant having more colorful flowers than the variety "Diamond Jubilee," but having the same long-lasting quality and generally similar plant habits as that variety. This objective was fully achieved, as evidenced by the fact that my new variety bears flowers of a form corresponding to those of "Diamond Jubilee;" the buds are Spinel Pink color overcast with Thulite Pink; the open flowers have a general color tonality of Pale Ochraceous Salmon, shaded with Thulite Pink and with a suffusion of Pale Yellow Orange extending from the base of each petal over the lower half thereof; the flowers have excellent long-lasting characteristics both on the bush and when cut; and the number of petals of each flower is considerably increased as compared with the flowers of "Diamond Jubilee," yet the keeping qualities of the latter are preserved in the new variety.

Asexual reproduction of my new variety by budding at Newark, New York, and at Pleasanton, California, shows that the foregoing characteristics and distinctions come true to form and are established and transmitted through succeeding propagations.

The accompanying drawing shows typical specimens of the flowers, stems and foliage of my new variety in different stages of development.

The following is a detailed description of my new variety, with color terminology in accordance with Ridgway's Color Standards and Nomenclature:

Parentage: Seedling.

*Seed parent.*—An unnamed seedling of "Diamond Jubilee."

*Pollen parent.*—"Serenade."

Classification:

*Botanic.*—Hybrid tea.

*Commercial.*—Hybrid tea.

*Flower*

(Observations made in a field at Newark, New York, in the latter part of the month of June, and in the early afternoon.)

Blooming habit: Recurrent; continuous.

Bud:

*Size.*—Large.

*Form.*—Globular; is not affected by wet or hot weather.

*Color.*—When sepals first divide—Van Dyke Red, Plate 13. When petals begin to unfurl—Spinel Red, Plate 26. When half blown—inside of petals: Spinel Pink, Plate 26, overcast with Thulite Pink, Plate 26; Reverse of petals: pale Ochraceous Buff, Plate 15, lightly shaded with Eosine Pink, Plate 1, and with Pinard Yellow, Plate 4 overcasting the lower half of the petal.

*Sepals.*—Branched; "hood" above bud; curl back when petals begin to unfurl. Color: inside—Kildare Green, Plate 31; Outside—Light Bice Green, Plate 17.

*Calyx.*—Color—Light Bice Green, Plate 17. Shape — apple. Size — large. Aspect — smooth. Odor when rubbed—none.

*Peduncle.* — Length — medium. Aspect — smooth. Color—Lettuce Green, Plate 5. Strength—erect; slender.

*Opening.*—Opens up well; is not affected by adverse weather conditions.

Bloom:

*Size.*—Large; average size when fully expanded—4½ inches to 5 inches.

*Borne.*—Singly and several together.

*Stems.*—Medium length; strong.

*Form.* — When first open — full. Permanence—outer petals curl back.

*Petalage.*—Double (full but open center). Number of petals under normal conditions—40 to 50.

*Color.*—Center of flower—Begonia Rose, Plate 1, lightly overcast with Spinel Pink, Plate 26. Outer petals—Light Buff, Plate 15, lightly overcast with Cameo Pink, Plate 26. Base of petals (aiglet)—Citron Yellow, Plate 16. Inside of petals—Pale Ochraceous Salmon, Plate 15, shaded with Thulite Pink, Plate 26, and with a suffusion of Pale Yellow Orange, Plate 3, extending from the base of the petal over the lower half of the petal. Reverse of petals—Shrimp Pink, Plate 1, shaded with Cameo Pink, Plate 26, and with a suffusion of Pale Yellow Orange, Plate 3, extending from the base of the petal over the lower half of the petal. General tonality from a distance—Pale Ochraceous Salmon, Plate 15, shaded with Thulite Pink, Plate 26.

*Discoloration.*—General tonality at end of first day—Pale Ochraceous Salmon, Plate 15, shaded with Thulite Pink, Plate 26. Second day—Pale Ochraceous Salmon, Plate 15, shaded with Cameo Pink, Plate 26. Third day—Light Buff, Plate 15, shaded with Cameo Pink, Plate 26.

Petals:

*Texture.*—Soft; is not affected by wet or hot weather.

*Appearance.* — Inside — shiny; outside — satiny.

*Form.*—Oval; slightly notched.

*Arrangement.*—Informal (with "rags" in center).

*Petaloids in center.*—Many; small.

*Persistence.*—Drop off cleanly.

*Fragrance.*—Strong. Nature—spicy, fruity fragrance.

*Lasting quality.*—On the plant and as cut flower—long.

*Genital organs*

Stamens, anthers: Large; many.

*Color.*—Apricot Yellow, Plate 4.

*Arrangement.*—Regular around styles.

Stamens, filaments (threads).—Long. Color—Pinard Yellow, Pate 4.

Pollen: Color—Baryta Yellow, Plate 4.

Styles: Columnar; uneven length; medium length; thin.

Stigmas: Color—Citron Yellow, Plate 16.

Ovaries: All enclosed in calyx.

Seeds: None.

*Plant*

Form: Bush.

Growth: Vigorous; upright.

Foliage: 5 to 7 leaflets.

*Size.*—Large.

*Quantity.*—Normal abundance.

*Color.*—New foliage: upper side—Victoria Lake, Plate 1; under side—Yellowish Oil Green, Plate 5, overcast with Victoria Lake, Plate 1. Old foliage: upper side—Spinach Green, Plate 5; under side—Light Cress Green, Plate 31.

*Shape.*—Oval pointed.

*Texture.* — Upper side — leathery. Under side—smooth.

*Ribs and veins.*—Prominent.

*Edge.*—Serrated (saw-toothed).

*Serration.*—Double; small.

*Leaf stem.*—Color—Cress Green, Plate 31. Under side—prickles.

*Stipules.*—Medium length; smooth.

Wood:

*New wood.*—Color—Yellowish Citrine, Plate 16, lightly overcast with Victoria Lake, Plate 1. Bark—smooth.

*Old wood.*—Color — Ivy Green, Plate 5. Bark—smooth.

Thorns:

*Thorns.*—Quantity—on main stalks from base and on laterals from stalk—ordinary. Form — narrow base; medium length; hooked downward. Color when young—Eugenia Red, Plate 13. Postion—irregular.

*Prickles.*—Quantity—on main stalks and on laterals—none.

*Short needles.*—Quantity—on main stalks and on laterals—none.

I claim:

A new and distinct variety of rose plant of the hybrid tea class, substantially as herein shown and described, characterized particularly as to novelty by having substantially the same relatively long-lasting quality of the blooms and the same general plant habits as the variety "Diamond Jubilee" (Plant Patent No. 824), but having more colorful buds and open blooms and more numerous petals than those of "Diamond Jubilee."

EUGENE S. BOERNER.

No references cited.